United States Patent
West, Jr.

(10) Patent No.: US 7,235,078 B2
(45) Date of Patent: Jun. 26, 2007

(54) PROTECTIVE DEVICES FOR USE WITH ANGLED INTERFERENCE SCREWS

(75) Inventor: Hugh S. West, Jr., Salt Lake City, UT (US)

(73) Assignee: HS West Investments LLC, Salt Lake City, UT (US)

( * ) Notice: Subject to any disclaimer, the term of this patent is extended or adjusted under 35 U.S.C. 154(b) by 499 days.

(21) Appl. No.: 10/304,719

(22) Filed: Nov. 26, 2002

(65) Prior Publication Data

US 2004/0102780 A1    May 27, 2004

(51) Int. Cl.
A61B 17/56 (2006.01)
A61F 2/30 (2006.01)
A61F 2/08 (2006.01)

(52) U.S. Cl. ............... 606/73; 623/13.14; 411/310
(58) Field of Classification Search .......... 606/72, 606/73, 104; 411/402, 403, 310, 383; 623/13–14
See application file for complete search history.

(56) References Cited

U.S. PATENT DOCUMENTS

| | | | |
|---|---|---|---|
| 2,852,056 A * | 9/1958 | Rapata ............... 411/304 |
| 3,942,406 A * | 3/1976 | Egner ............... 411/418 |
| 3,974,621 A * | 8/1976 | Stang ............... 411/75 |
| 4,059,102 A | 11/1977 | Devas |
| 4,175,555 A * | 11/1979 | Herbert ............... 606/73 |
| 4,456,005 A * | 6/1984 | Lichty ............... 606/60 |
| 4,507,817 A * | 4/1985 | Staffeld ............... 7/158 |
| 5,062,843 A | 11/1991 | Mahony, III |
| 5,139,499 A | 8/1992 | Small et al. |
| 5,151,104 A | 9/1992 | Kenna |
| 5,167,664 A * | 12/1992 | Hodorek ............... 606/73 |
| 5,234,430 A * | 8/1993 | Huebner ............... 606/60 |
| 5,259,398 A | 11/1993 | Vrespa |
| 5,282,802 A | 2/1994 | Mahony, III |
| 5,324,308 A * | 6/1994 | Pierce ............... 606/232 |
| 5,336,225 A | 8/1994 | Zang |
| 5,364,400 A | 11/1994 | Rego, Jr. et al. |
| 5,425,733 A * | 6/1995 | Schmieding ............... 606/104 |

(Continued)

FOREIGN PATENT DOCUMENTS

EP    1 101 459 A2    5/2001

OTHER PUBLICATIONS

"Tri-Cortical ACL Soft Tissue Graft Fixation", Arthrex. Published at least as early as Oct. 2001.

Primary Examiner—Anu Ramana
(74) Attorney, Agent, or Firm—Workman Nydegger

(57) ABSTRACT

A protective device for use with an interference screw used to attach a soft tissue graft within a bone tunnel reduces the tendency of the interference screw to undesirably snag a soft tissue graft and/or sutures when screwed into a bone tunnel. The protective device has an angled face that corresponds to an angled face of the interference screw and threads that correspond to the threads of the interference screw. When used together, the protective device effectively completes the part of the interference screw that is removed to form the angled face. This, in turn, reduces or eliminates any sharp edges that would otherwise catch or snag the tissue graft and/or sutures as the interference screw is screwed into a bone tunnel during a joint repair procedure. The protective device may be included within a kit together with a correspondingly sized and shaped interference screw, and optionally with a driver.

17 Claims, 5 Drawing Sheets

U.S. PATENT DOCUMENTS

| | | | |
|---|---|---|---|
| 5,470,334 A * | 11/1995 | Ross et al. ................... 606/72 |
| 5,505,731 A | 4/1996 | Tornier |
| 5,536,127 A | 7/1996 | Pennig |
| 5,607,428 A | 3/1997 | Lin |
| 5,632,748 A * | 5/1997 | Beck et al. ................... 606/89 |
| 5,653,710 A | 8/1997 | Härle |
| 5,690,489 A * | 11/1997 | Carchidi ................... 433/141 |
| 5,693,055 A * | 12/1997 | Zahiri et al. ................ 606/69 |
| 5,695,497 A * | 12/1997 | Stahelin ...................... 606/73 |
| 5,743,912 A | 4/1998 | Labille et al. |
| 5,904,685 A * | 5/1999 | Walawalkar ................. 606/73 |
| 5,925,048 A | 7/1999 | Ahmad et al. |
| 5,935,129 A * | 8/1999 | McDevitt et al. ............ 606/72 |
| 5,957,953 A * | 9/1999 | DiPoto et al. .............. 606/232 |
| 5,964,766 A | 10/1999 | Shaw |
| 5,964,768 A | 10/1999 | Huebner |
| 5,968,045 A | 10/1999 | Frazier |
| 5,984,966 A * | 11/1999 | Kiema et al. ............. 623/13.14 |
| 6,001,100 A | 12/1999 | Sherman et al. |
| 6,001,101 A | 12/1999 | Augagneur et al. |
| 6,010,507 A * | 1/2000 | Rudloff ........................ 606/72 |
| 6,015,410 A * | 1/2000 | Tormala et al. ............... 606/73 |
| 6,019,759 A | 2/2000 | Rogozinski |
| 6,030,162 A | 2/2000 | Huebner |
| 6,116,832 A * | 9/2000 | Wolf et al. ................. 411/383 |
| 6,296,641 B2 * | 10/2001 | Burkhead et al. ............. 606/61 |
| 6,361,258 B1 * | 3/2002 | Heesch ...................... 411/178 |
| 6,368,322 B1 * | 4/2002 | Luks et al. ................... 606/73 |
| 6,387,129 B2 * | 5/2002 | Rieser et al. ............. 623/13.14 |
| 6,471,707 B1 * | 10/2002 | Miller et al. .................. 606/73 |
| 6,517,543 B1 * | 2/2003 | Berrevoets et al. ........... 606/73 |
| 6,517,579 B1 * | 2/2003 | Paulos et al. ............ 623/13.14 |
| 6,533,791 B1 * | 3/2003 | Betz et al. ..................... 606/99 |
| 6,562,071 B2 * | 5/2003 | Jarvinen .................. 623/13.14 |
| 6,565,572 B2 * | 5/2003 | Chappius ..................... 606/73 |
| 6,632,245 B2 * | 10/2003 | Kim ........................ 623/13.14 |
| 6,736,847 B2 * | 5/2004 | Reay-Young et al. .... 623/13.14 |
| 6,916,321 B2 * | 7/2005 | TenHuisen et al. ........... 606/73 |
| 7,083,647 B1 * | 8/2006 | Sklar et al. .............. 623/13.14 |

\* cited by examiner

PROTECTIVE DEVICES FOR USE WITH ANGLED INTERFERENCE SCREWS

BACKGROUND OF THE INVENTION

1. The Field of the Invention

The present invention generally relates to the field of joint repair surgery, such as reconstruction of the anterior cruciate ligament (ACL). More particularly, the invention relates to the field of interference screws used generally for fixation of soft tissue grafts, such as tibial affixation of soft tissue ACL grafts.

2. The Relevant Technology

Injuries to joints, specifically the knee, are quite common, particularly when one engages in vigorous sporting activities. A common injury is a rupture or tear of the anterior cruciate ligament (ACL), which is the primary ligament responsible for holding the knee joint together and which keeps it from slipping out of joint or dislocating. An unrepaired ruptured or torn ACL can cripple, and would most certainly limit physical activity of, the person suffering a ruptured or torn ACL.

One method for performing an ACL reconstruction procedure involves taking a tissue graft from another part of the body, such as a soft tissue graft (e.g., from the hamstrings), and attaching it at both ends through bone tunnels drilled through the two bones that make up the knee joint: the femur and the tibia. When secured in place, the tissue graft mimics and, hence, takes the place of, the ACL itself. This tissue graft holds the femur and tibia together to make the joint more stable, while simultaneously allowing for normal joint movements (i.e., flexion and extension).

One way to attach the graft to the bone is with an interference screw. An interference screw is screwed into a bone tunnel through which the soft tissue graft passes, thereby causing the graft to be compressed against the surface of the bone tunnel with sufficient force for holding the graft in place. The interference screw shortens the effective length of the graft and minimizes the "bungee effect" by affixing the soft tissue graft and preventing the graft from stretching inside of the bone tunnels.

One type of interference screw includes a threaded body and a trailing end, or head, that is substantially flat and perpendicular relative to the threaded body. This can create a problem whenever the bone tunnel is formed at an angle relative to the bone surface. Because an angled bone tunnel is not perpendicular to the bone surface, the surface of the trailing end of the interference screw will not lie flush with the bone surface. As a result, either a corner of the trailing end will protrude from the bone, requiring an extra cutting step to remove the protrusion, or a substantial portion of the screw will be recessed within the bone tunnel surface, which reduces the amount of surface contact between the screw and the hard cortical bone at the bone surface, thereby potentially comprising the holding strength of the screw against the graft.

In order for the interference screw to make complete circumferential contact against the cortical bone region of the bone tunnel, an improved screw has been developed by the inventor having an obliquely angled trailing end that matches or corresponds to the angle of the bone tunnel. In this way, the trailing end can lie flush with the bone tunnel surface, while also making complete circumferential contact at the cortical bone region of the bone tunnel, when the screw has been inserted properly into the bone tunnel.

Interference screws of the inventor having obliquely angled trailing ends have proven to be an excellent solution to the problems inherent whenever a bone tunnel is angled so as to not be perpendicular to the bone tunnel surface. Nevertheless, forming an oblique angle in the trailing end of the interference screw can create relatively sharp edges, particularly where the threads are exposed, which can potentially snag the tissue graft and/or sutures attached to the graft when the screw is screwed into the bone tunnel. Accordingly, there is a present need to provide interference screws with angled trailing ends while minimizing the risk that the interference screw will snag the tissue graft and/or sutures as the screw is screwed into the bone tunnel.

SUMMARY OF THE INVENTION

The present invention is directed to protective devices for use with angled interference screws used to affix soft tissue grafts within angled bone tunnels during reconstructive surgery. The protective devices reduce or eliminate the tendency of angled interference screws from snagging the tissue graft and/or sutures as the interference screw is screwed into the bone tunnel. The invention also encompasses methods and kits that employ or include one or more protective devices in combination with one or more angled interference screws.

According to one embodiment, the protective devices of the invention are configured to engage interference screws that have angled faces or trailing ends while the interference screws are inserted into obliquely aligned bone tunnels. Each protective device generally comprises a threaded body having a central passage through which a drive shaft can be inserted and an angled surface that mates with the angled surface of the interference screw. In this way, the protective device essentially completes the interference screw (i.e., it fills in the portion of the screw that is removed to form the angled trailing end).

The protective device temporarily forms an interference screw/mating device combination that virtually eliminates any sharp edges associated with the angled trailing end of the interference screw. This, in turn, reduces the risk that the interference screw will snag the tissue graft and/or sutures when screwed into the bone tunnel to secure a tissue graft in place.

According to one aspect of the invention, the protective device includes threads having the same pitch and spacing as the threads on the interference screw. Accordingly, when the protective device is aligned with the interference screw, and when the angled faces of the mating device and the interference screw are in mating engagement, the threads of the protective device will be substantially aligned with the threads of the interference screw. In this way, the protective device will temporarily complete the thread pattern of the portion of the interference screw that is removed to form the angled trailing end. Completing the thread pattern allows the interference screw to be threadably inserted into the bone tunnel without unnecessarily exposing the discontinuous threads that are disposed along the angled face of the interference screw to the surrounding tissues. This, in turn, facilitates placement of the interference screw within the bone tunnel, particularly when pressing the tissue graft against the bone tunnel wall. Notwithstanding the foregoing, it is also within the scope of the invention to provide protective devices that are unthreaded although this embodiment is not presently preferred.

In many cases, the surgeon may have interference screws of varying size and/or shape at his or her disposal to accommodate differences in the size and/or angle of different bone tunnels formed within different patients. In such cases, it may be advantageous to provide a variety of protective devices that correspond to the variously sized and/or shaped interference screws. In this way, the surgeon will be able to select a protective device that best fits or mates with a particular interference screw being used.

In an alternative embodiment, it may be desirable to provide one or more protective devices that are adjustable so as to accommodate interference screws of various size and/or shape. For example, a protective device within the scope of the invention may be spring loaded or otherwise able to expand or contract depending on the size of the interference screw. A locking device may be provided that locks the protective device into a desired size or configuration.

These and other advantages and features of the present invention will more fully apparent from the following description and appended claims, or learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

The invention relates to protective devices for use with angled interference screws used to affix soft tissue grafts within angled bone tunnels during reconstructive surgery. The invention also relates to methods and kits that comprise one or more protective devices in combination with one or more angled interference screws.

Reference will now be made to figures wherein like structures will be provided with like reference designations.

Figure 1:
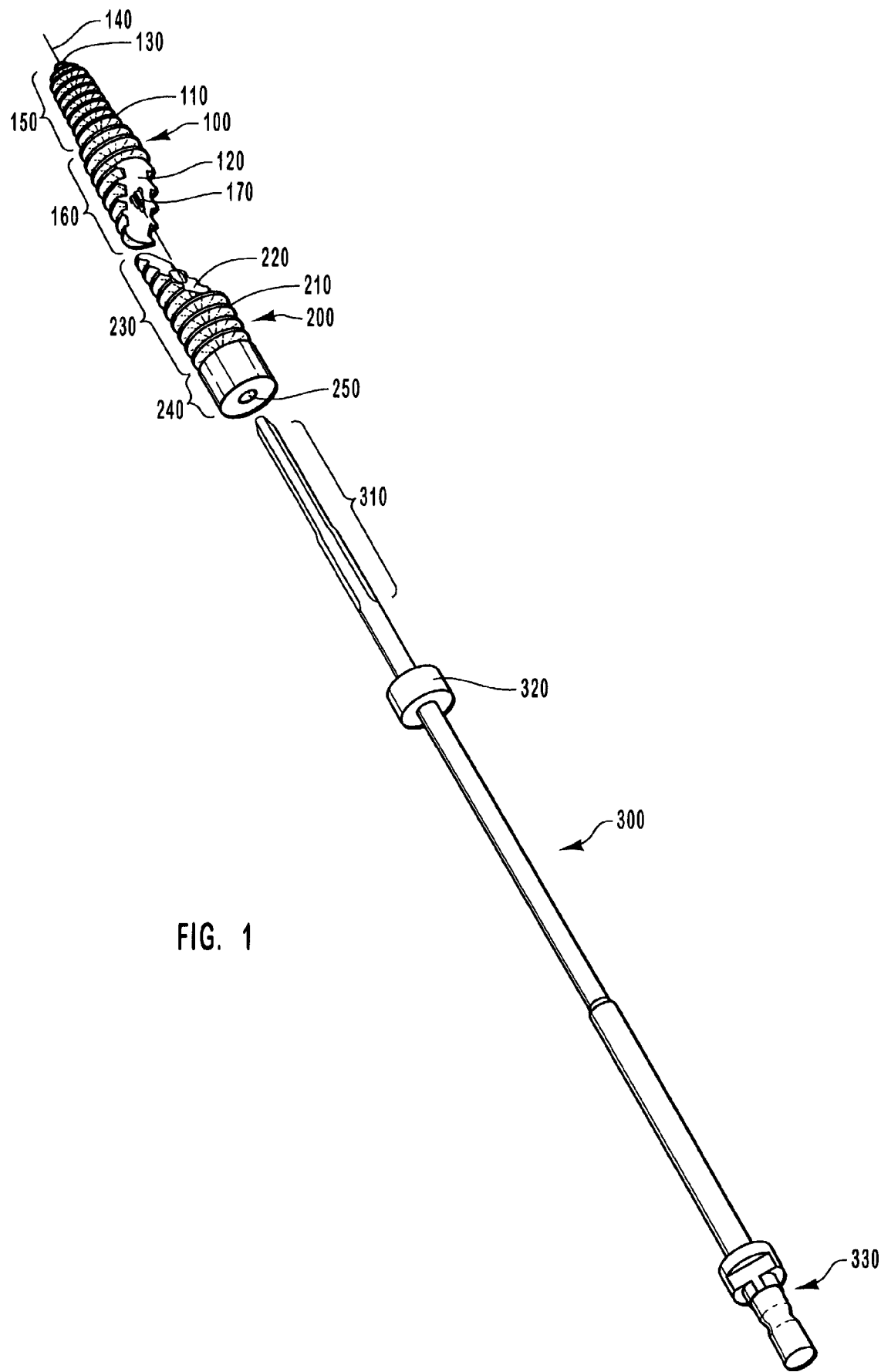
FIG. 1 is an exploded view of an angled interference screw, an exemplary protective device according to the invention, and a driving instrument used to screw the interference screw into a bone tunnel.
Figure 2:
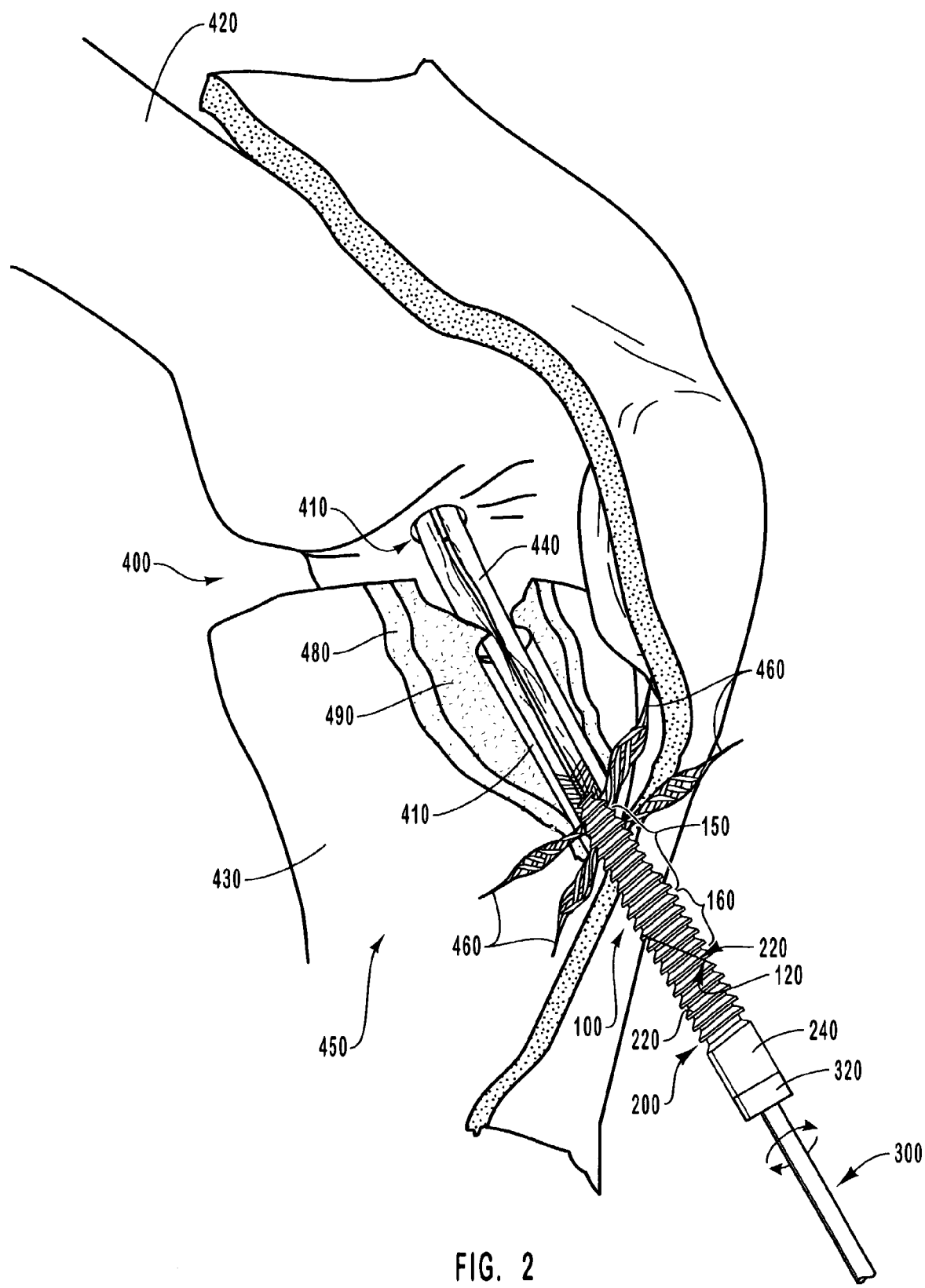
FIG. 2 is a perspective view of a knee joint that includes a femur, a tibia, and an angled bone tunnel fashioned through the tibia and femur, together with a soft tissue graft inserted through the bone tunnel and an interference screw being inserted into the bone tunnel while mated with a protective device according to the invention.

Reference is first made to FIG. 1, which is an exploded view of an exemplary interference screw 100, an exemplary protective device 200, and an exemplary driver 300. FIG. 2 depicts the interference screw 100, exemplary protective device 200, and exemplary driver 300 in use to secure a soft tissue graft 440 within a bone tunnel 410. Before discussing how the various components work together to reduce the tendency of the interference screw to snag the graft and/or sutures when screwed into the bone tunnel, various features and embodiments relating to the interference screw will now be given.

Angled interference screws that may be used in combination with protective devices according to the invention are described in co-pending U.S. application Ser. No. 09/977,154, filed Oct. 12, 2001, now U.S. Pat. No. 6,953,463, in the name of Hugh S. West, Jr., M.D., and entitled IMPROVED INTERFERENCE SCREW HAVING INCREASED UPPER DIAMETER. For purposes of disclosing angled interference screws, the foregoing U.S. application is incorporated by reference.

In general, angled interference screws comprise a threaded body that extends between a proximal end and a distal end along a central axis. Virtually any interference screw known in the art can be modified so as to have an angled trailing end. In one embodiment, the threaded body may include proximal and distal threaded sections having differing diameters, with the proximal section having a larger average diameter than the distal section. The proximal and distal threaded sections may comprise constant diameters, such that the outer diameter of each section is substantially cylindrical, or they may have varying diameters such that at least part of each section includes a taper (i.e., is angled rather than parallel to the central axis). One threaded section may be cylindrical and the other section at least partially tapered.

The proximal threaded section includes an angled face, preferably corresponding to the angle of the bone tunnel into which the interference screw is to be inserted. In this way, the angled face will be able to lie approximately flush with the bone surface surrounding the bone tunnel, or at least lie parallel thereto. This reduces or eliminates any significant protrusion by the interference screw above the bone surface when completely inserted within the bone tunnel during fixation of a soft tissue graft, while maintaining contact with substantially all of the cortical bone defining the bone tunnel wall.

Angled interference screws can have any thread pattern. In one embodiment, the thread pattern will comprise a single continuous thread having a uniform pitch wrapping around the outer perimeter of the threaded body. The distal tip, particularly if tapered, may or may not be entirely threaded. The thread or threads may have a constant thread depth (i.e., the radial distance between the outer edge and root of the thread) throughout at least a portion of the screw, although the thread depth may vary at the distal end if tapered, and it may vary, if desired, at the transition between the distal and proximal threaded sections.

It is also within the invention to provide interference screws that include no threads along a particular length of screw about the circumference (e.g., discontinuous threads), such as a non-threaded transition section between the proximal and distal threaded sections, a non-threaded distal tip, or a non-threaded section at the proximal end. It is also within the scope of the invention to provide interference screws of varying thread pitch.

As shown in FIGS. 1 and 2, the exemplary interference screw 100 comprises a threaded body 110 axially extending between an angled face 120 and a tip 130 along a central axis 140. The tip 130 may advantageously be tapered as illustrated in order to facilitate entry of the interference screw 100 into a bone tunnel.

Inasmuch as the interference screw 100 is inserted into a patient's body, the interference screw preferably comprises a material composition that is biodegradable, biocompatible and/or biointegratable. According to one preferred embodiment, the interference screw comprises polyl-l-lactic acid (PLLA). It will be appreciated, however, that the interference screw may alternatively comprise other suitable materials, such as bio-compatible plastics and bio-compatible metals, including but not limited to titanium or stainless steel.

According to one embodiment, the angled face 120 of the interference screw 100 is preferably angled or aligned relative to the central axis 140 in order to correspond or be compatible with the angle of the bone tunnel relative to the bone surface. This will enable the angled face 120 of the interference screw 100 to lay substantially flush with the bone surface surrounding a bone tunnel when the screw 100 is completely inserted into the bone tunnel and oriented at an appropriate rotational angle. In the case of ACL repair surgery, the bone tunnel will usually have an angle in a range of about 20° to about 60° relative to the bone surface, preferably in a range of about 30° to about 40°, and more preferably, in an angle of about 35°. The angled face 120 of the interference screw 100 will have an angle that matches or corresponds to this angle in order to lie substantially flush, or at least parallel, to the bone surface when inserted into a bone tunnel. In general, the angle of the angled face 120 will have an angle relative to the central axis 140 that has the same magnitude as the angle of the bone tunnel relative to the bone surface.

The exemplary threaded body 110 of the interference screw 100 comprises a distal threaded cylindrical section 150 and a proximal threaded cylindrical section 160. As shown in FIGS. 1 and 2, the threads of the distal and proximal cylindrical sections 150 and 160 have the same pitch, although this is not required. The threads of the distal and proximal cylindrical sections 150 and 160 are also shown as being joined as a single continuous thread, although this is not required.

The diameter of the distal threaded cylindrical section 150 next to the tapered tip 130 is smaller than the diameter of the proximal threaded cylindrical section 160. The term "diameter" as used herein will generally refer to the outer diameter defined by the outer edge of the threads, although it will also refer to twice the radius in the case where a portion of the screw has been removed or omitted, such as in the case of an obliquely angled face. According to one embodiment, the diameter of the distal threaded cylindrical section 150 is within a range of about 9 mm to about 11 mm, and the diameter of the proximal threaded cylindrical section 160 is within a range of about 10 mm to about 12 mm. In one embodiment, the diameter of the distal cylindrical section 150 is approximately 1 mm less than the diameter of the proximal cylindrical section 160. A tapered transition section may be provided to join the distal cylindrical section 150 with the proximal cylindrical section 160 with a smooth transition.

The variation in diameter between the distal threaded section 150 and the proximal threaded section 160 enables the interference screw 100 of the invention to securely compress a soft tissue graft against the cortical bone region of a bone tunnel while, at the same time, applying less pressure against the soft tissue graft within the cancellous bone region of the bone tunnel. This is beneficial for enabling the soft tissue graft to more quickly heal and bond with the bone in the cancellous bone region, while providing increased holding strength of the soft tissue graft by the interference screw against the hard cortical bone region.

It will be appreciated that the length of the interference screw 100 may comprise any desired length for accommodating various needs and preferences.

As shown, the interference screw 100 also includes an exemplary drive socket 170. The drive socket 170 is advantageously configured for receiving the shaft 310 of a driver 300 that can rotatably screw the interference screw 100 into a bone tunnel. As shown, the exemplary drive socket 170 comprises a shape that is configured for receiving the shaft 310 of a typical interference screw driver 300 that includes three radially extending protrusions.

The drive socket 170 is preferably aligned with the central axis 140 of the interference screw 100 and may extend to any desired depth within the interference screw 100. In particular, the drive socket 170 may be configured to extend only partially into the interference screw 100 or, alternatively, to extend all the way through the proximal section 160 and into the distal section 150 of the interference screw 100. The drive socket 170 may also extend all the way through the proximal and distal sections 150 and 160. An axial bore (not shown) may be provided for a guide wire, as will be understood by those skilled in the art.

The exemplary protective device 200 is configured for use with the exemplary interference screw 100. In particular, the protective device 200 is configured to concentrically align with the interference screw 100 along central axis 140 and to engage the interference screw 100 along its angled face 120. In one embodiment, the protective device 200 includes an angled face 220 that is sized and shaped so as to planarly engage the angled face 120 of the interference screw 100, as shown and described below in more detail in reference to FIG. 2. In the alternative, the angled faces 120 and 220 may be nonplanar, such as having complementary shapes or curvatures that are able to mate or otherwise interact in a desired fashion.

To accommodate the angle of the angled face 120 of the interference screw 100, the protective device 200 includes an angled face 220 that has an angle relative to the central axis 140 that corresponds to or complements the angle of the angled face 120 of the interference screw 100. For example, the angles of the angled faces 120 and 220 may be selected so that they add up to 90° when using angles that have been normalized to between 0–90° (e.g., angles between 90–180° are "normalized" by subtracting the angle from 180°). Thus, if the angle of angled face 120 of the interference screw 100 were 30° relative to the central axis, the corresponding angle of the angled face 220 of the protective device 200 would be 60°. In this way, the angled faces 120 and 220 will lie flush together and the interference screw 100 and protective device 200 will be concentrically aligned.

With respect to the preferred angles mentioned above relating to interference screws suitable for use in ACL repair procedures, the angled face 220 of the protective device 200 will have a normalized angle that is preferably in a range of about 30° to about 70° relative to the central axis 140, more preferably in a range of about 50° to about 60°, and most preferably about 55° relative to the central axis 140.

Because the protective devices according to the invention are used for inserting an interference screw 100 within the body, they may comprises any material that is safe when temporarily contacted with a person's body. Because it is not intended for the protective devices to remain embedded within a patient's body, it is not necessary for them to have the same level of biocompatibility as the interference screw. Nevertheless, it is within the scope of the invention for the protective device to comprise (PLLA), Teflon (polytetrafluoroethylene (PTFE)), stainless steel, titanium or other materials used to make the interference screw.

The length of the protective device may vary to accommodate the size of various interference screws and driving instruments. The protective device is preferably long enough that it can mate with the face of the interference screw at the same time that both are being engaged by the driving instrument. To accommodate various lengths of protective device 200, however, a driving instrument 300 may be configured with an adjustable collar 320 that can be selectively positioned and repositioned as desired at various locations along the shaft 310 of the driving instrument 300. The collar 320 can be configured, for example, with an allan wrench locking/releasing screw (not shown), or any other suitable locking means.

The diameter of the protective device 200 may also vary. In one embodiment, the diameter of the protective device 200 is at least as large as the diameter of the proximal threaded cylindrical section 160 of the interference screw 100. Accordingly, the diameter of the protective device 200 has a diameter of at least about 10 mm.

As shown in FIG. 1, the body 210 of the protective device 200 includes a passageway 250 through the body 210 of the protective device 200 along the central axis 140. This passageway 250 is preferably large enough to allow the shaft 310 of the driving instrument 300 to pass through it. The passageway 250 may be configured so as to enable the driving instrument to slidably engage the protective device 200 or to pass through the protective device 200 without engaging it. The embodiment in which the passageway 250 does not engage the shaft 310 allows the protective device 200 to freely rotate about the shaft 310 of the driving instrument 300. This can be useful for allowing the protective device 200 to be rotated about the shaft 310 until it is properly aligned with the interference screw 100 so that it can mate with or otherwise engage the angled face 120 of the interference screw 100.

In one embodiment, the passageway 250 through the protective device 200 is sized and shaped so as to mechanically engage the shaft 310 of the driving instrument 300 in a limited number of alignments. This embodiment helps ensure that the protective device 200 is properly aligned with the interference screw 100. For example, the passageway 250 may have the same cross-sectional shape as the drive socket 170 of the interference screw 100.

According to one aspect of the invention, the protective device 200 may include a threaded portion 230 and an extension 240. The extension 240 may be non-threaded, as shown, or threaded if desired. It is generally configured to receive the compressive forces applied by a driving instrument 300, as described above, particularly the collar 320.

The threaded portion 230 of the protective device 200 is configured with threads having the same pitch and general configuration as the threads disposed on the proximal portion 160 of the interference screw 100. This allows the discontinuous threads that are exposed along the face 120 of the interference screw 100 to align with the discontinuous threads that are disposed along the face 220 of the protective device 200. Having the threads of the two devices mate better shields the edges of the threads of the interference screw 100, which would otherwise be exposed in the absence of the protective device 200.

The protective devices according to the invention may be manufactured independently of the interference screws or they may be manufactured integrally with the interference screws. If manufactured integrally with a corresponding interference screw, the interference screw and protective device can simply be cut apart, thereby ensuring that the angled face of the interference screw will match the angled face of the protective device. In this embodiment, the thickness of the cutting blade or other device used to separate the protective device from the interference screw is preferably not so great as to remove too much material (kerf), thereby creating a discontinuity in the threads at the point of contact between the interference screw and the protective device.

Turning specifically now to FIG. 2, the use of the protective device 200 in combination with an interference screw 100 is illustrated. By way of background, FIG. 2 shows a partial cross-sectional view of a knee joint 400. A bone tunnel 410 is formed at an angle into or through the femur 420 and through the tibia 430 of the knee joint 400. The bone tunnel 410 formed through the tibia 430 is preferably formed at an angle within a range of about 30° to about 40° relative to the bone surface.

During ACL reconstructive surgery, according to one embodiment, a soft tissue graft 440 is inserted through the bone tunnel 410 of the femur 420 and the tibia 430. According to the one embodiment, the soft tissue graft 440 comprises a hamstring graft. Hamstring grafts typically comprise multiple strands (e.g. four strands) and are well known in the art for ACL repair operations. Although a multi-strand hamstring graft may be used in the present example as one suitable soft tissue graft, it will be appreciated that the interference screws of the invention may be used to affix other appropriate soft tissue grafts comprising any number of strands (e.g., one or more strands taken from the patellar tendon). In appropriate circumstances an interference screw may be used to affix bone-tendon-bone or other grafts.

The soft tissue graft 440 is initially passed through the tibial portion of the bone tunnel 410 and secured within the bone tunnel 410 of the femur 420 with an interference screw or other device. Next, the soft tissue graft 440 is pulled through the bone tunnel 410 within the tibia 430 and then properly tensioned to ensure that the graft 440 is ultimately secured with the correct amount of tension. Any suitable graft tensioning device may be employed. An example of a tensioning device that is especially suitable for independently tensioning multiple stranded tissue grafts is described in U.S. application Ser. No. 09/711,488, filed Nov. 13, 2000 now U.S. Pat. No. 6,679,889, in the name of Hugh S. West, Jr., M.D., and entitled APPARATUS AND METHODS FOR INDEPENDENTLY CONDITIONING AND PRE-TENSIONING A PLURALITY OF LIGAMENT GRAFTS DURING JOINT REPAIR. For purposes of disclosing soft tissue graft tensioning devices, the foregoing U.S. application is incorporated herein by reference.

Once the soft tissue graft 440 has been properly tensioned, the soft tissue graft 440 can be secured to the tibia 430. An interference screw according to the present invention may be used to secure the soft tissue graft 440 within the bone tunnel 410 of the tibia 430, thereby reducing the effective length and elasticity of the soft tissue graft 440.

In one embodiment, the ends 460 of the soft tissue graft 440 are tied, such as with a whip stitch, and pulled apart so that an interference screw, such as interference screw 100, may be inserted within the bone tunnel 410 between the separate strands of the soft tissue graft 440. Alternatively, the graft 440 may be positioned eccentrically within the bone tunnel 410. Once the interference screw 100 has been properly positioned, a driving instrument, such as driving instrument 300, can be used to screw the interference screw 100 into the bone tunnel 410 within the tibia 430. The driving instrument 300 can be rotated, in order to screw the interference screw 100 into the bone tunnel 410, by rotating the driving engagement portion 330 (FIG. 1) of the driving instrument 300 with a handle, motorized drive, or other suitable driving device.

The interference screw 100 is used in combination with the protective device 200 in order to shield the discontinuous threads disposed along the edges of the face 120 of the interference screw 100. This, in turn, reduces or eliminates the tendency of the thread of the interference screw 100 to snag or engage the tissue graft 440 or sutures in an undesirable fashion. As shown in FIG. 2, the face 210 of the protective device 200 is planarly engaged with the face 120 of the interference screw 100. The threads of protective device 200 are also aligned with the threads of the interference screw 100. Accordingly, as the interference screw 100 is screwed into the bone tunnel 410, the edges of the angled face 120 are shielded by the face 220 of the protective device 200 so that they will not catch on the ends 460 of the tissue graft 440 and/or sutures connected to the graft 440.

Although the protective device 200 depicted in FIGS. 1 and 2 is sized and configured to mate with interference screw 100 having a corresponding size and shape, it is within the scope of the invention to provide protective devices (not shown) that can be adjusted so as to accommodate a plurality of interference screws of various sizes and/or shapes. For example, protective devices within the scope of the invention may be spring loaded or otherwise able to expand or contract depending on the size of the interference screw. A locking device may be provided that locks the protective device into a desired size or configuration.

Figure 3:
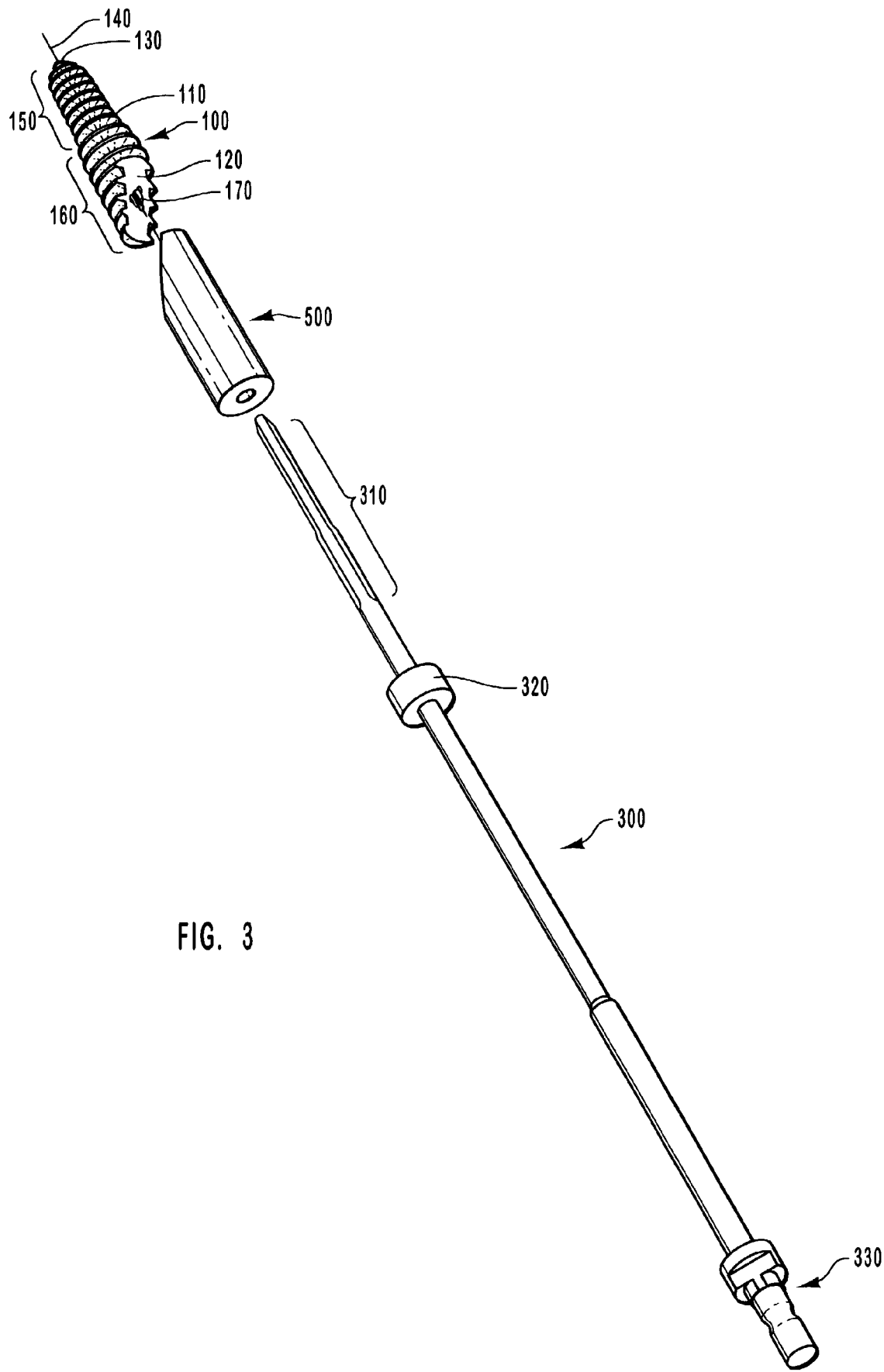
FIG. 3 is a perspective view of an unthreaded protective device according to the invention in a mating configuration relative to an interference screw.

It is also within the scope of the invention to provide unthreaded protective devices. FIG. 3 illustrates the use of an unthreaded protective device 500 that is able to mate with the interference screw 100 in much the same way as the threaded protective device 200 described above (i.e., by abutting the angled face 120 of the interference screw 100). The main difference is that the unthreaded protective device 500 does not complete the thread pattern of the inference screw 100. Instead, the unthreaded protective device 500 substantially completes the shape of the interference screw in order to occupy the otherwise open space extending from the angled face 120. In this way, the unthreaded protective device 500 will help to prevent or inhibit a soft tissue graft or sutures from becoming snagged by the exposed edge of the inference screw 100 in the vicinity of the angled face 120.

Figure 4:
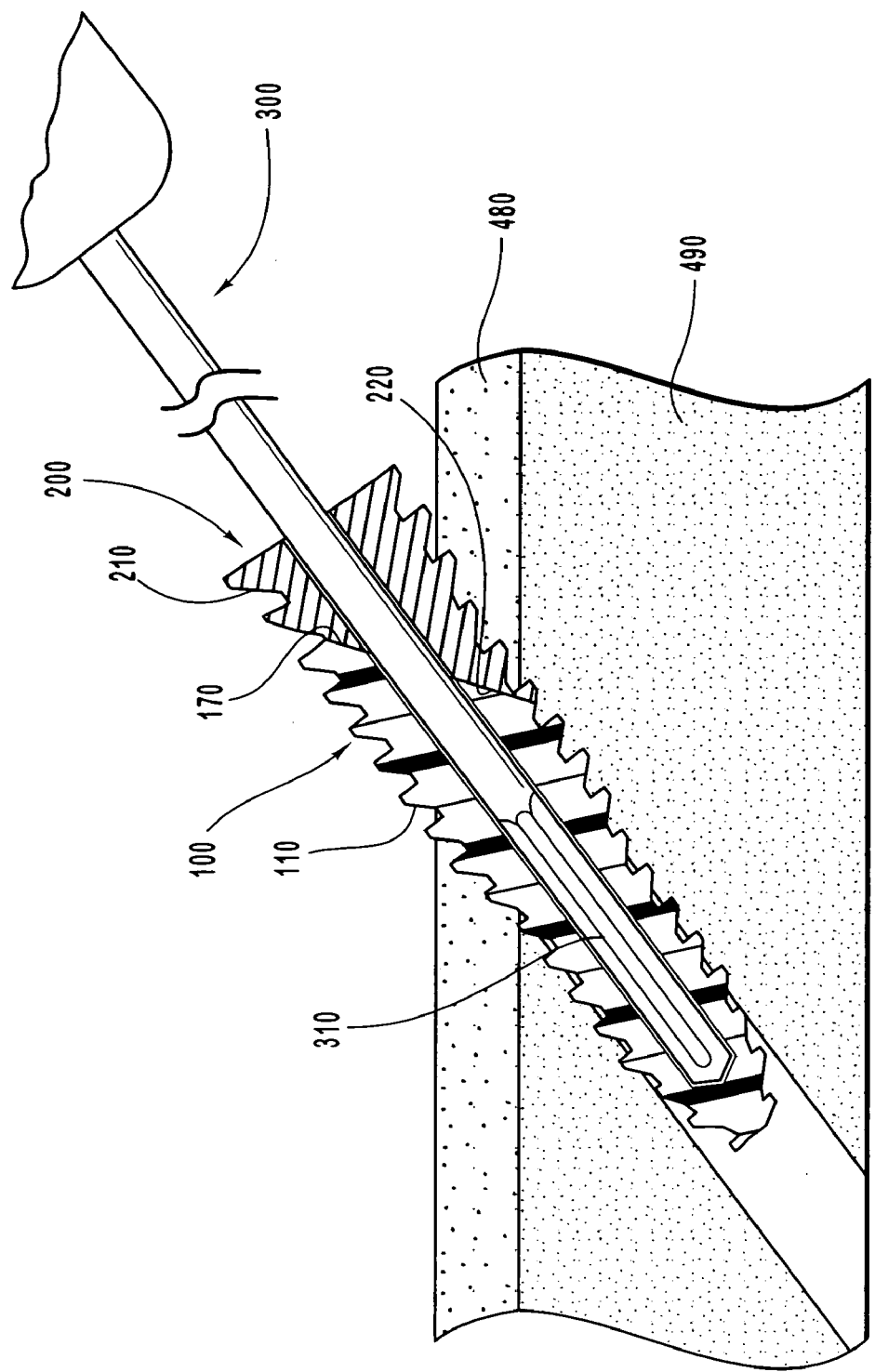
FIG. 4 is a cross-sectional view of an interference screw-protective device combination being inserted into an angled bone tunnel, with the interference screw being one half turn out of alignment relative to the bone tunnel so that the angled faces of the interference screw and protective device do not lie flush with the surrounding bone surface.
Figure 5A:
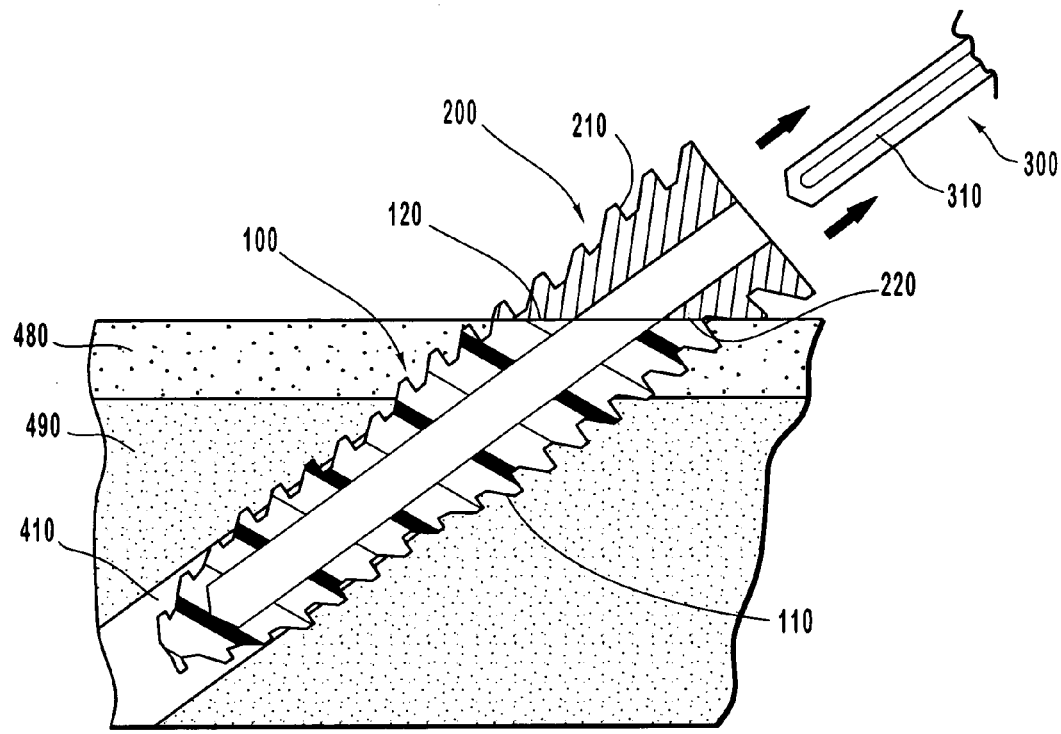
FIG. 5A is a cross-sectional view of the interference screw-protective device combination of FIG. 4 after having been rotated into proper alignment relative to the bone tunnel so that the angled faces of the interference screw and protective device both lie flush with the surrounding bone surface.
Figure 5B:
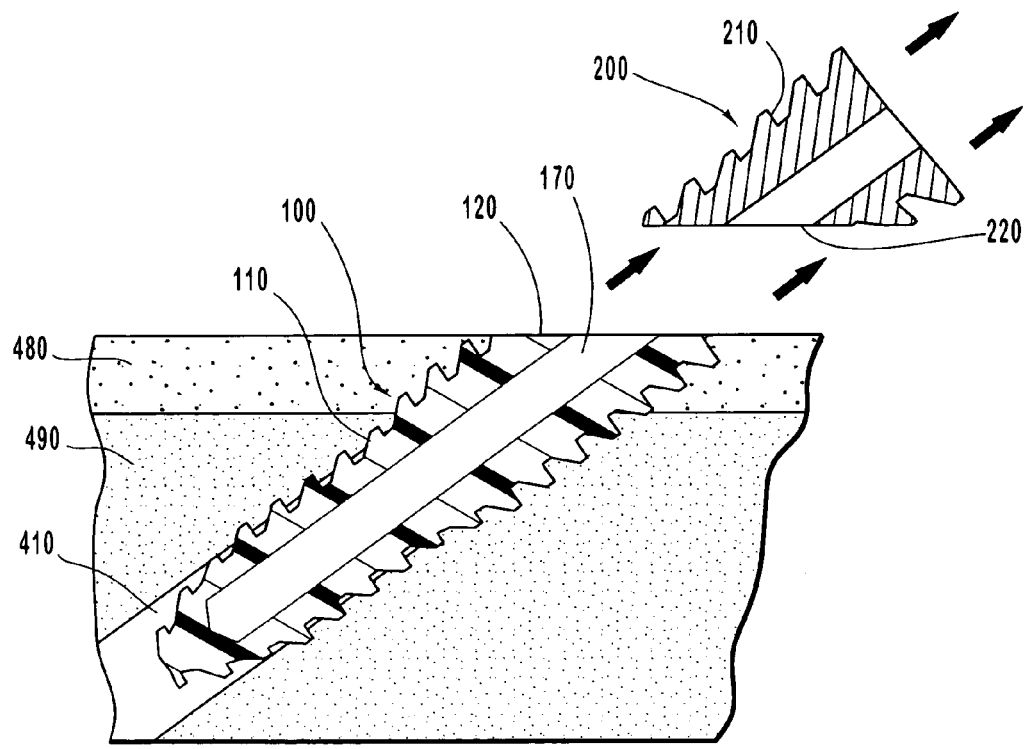
FIG. 5B is a cross-sectional view of the properly aligned interference screw of FIG. 5A and the protective device being separated from the interference screw.

Depending on the tightness of the fight between the inference screw 100 and a bone tunnel into which it is to be placed, it may be beneficial in same cases for the unthreaded protective device 500 to have a diameter that is less than the diameter of the inference screw 100 in order to facilitate the temporary entry of the protective device 500 into the bone tunnel during placement of the interference screw. Aside from lacking threads, the unthreaded protective device 500 is in other respects the same or similar to the threaded protective device 200 described above. The temporary entry of a protective device (albeit threaded) is illustrated in FIGS. 4 and 5A. FIG. 4 shows what happens when an interference screw having an obliquely angled face is one half turn out of alignment relative to the bone tunnel. In this position, a portion of a protective device mated with the interference screw inherently lies (temporarily) within the bone tunnel as illustrated. FIG. 5A (derived from FIG. 4 of U.S. Pat. No. 6,953,463, which was previously incorporated by reference) shows the same interference screw after having been rotated one half turn into proper alignment with the bone tunnel. In this position, both the angled face of the interference screw and the angled face of the protective device lie flush with the bone surface. In this position, the protective device no longer lies within the bone tunnel and can be easily separated from the interference screw as illustrated in FIG. 5B.

It is within the scope of the invention to singly provide one or more of the protective devices as needed to facilitate insertion of an angled interference screw into a bone tunnel. In addition, one or more protective devices may be included together with one or more interference screws within a kit, optionally in combination with one or more driver devices. Kits that comprise differently sized and/or shaped interference screws may comprise a plurality of correspondingly sized and shaped protective devices in order to provide a protective device that is able to mate with each interference screw. Alternatively, kits may comprise differently sized and/or shaped interference screws together with one or more protective devices that are adjustable so as to accommodate various interference screws within the kit.

In summary, the protective devices of the invention are configured help place interference screws into bone tunnels and, more particularly, to help place angled interference screws into bone tunnels in a way as to prevent the edges of the interference screw face from catching or snagging a tissue graft and/or sutures attached to the graft and/or other tissues or structures present at the surgical site.

The protective devices may be configured with various diameters, lengths, thread pitch, and face angles to accommodate variations in the corresponding interference screws. The protective devices may be sold separately from the interference screws or sold as part of a kit comprising an interference screw and a corresponding protective device. The kit may also include a driving instrument configured for use with the interference screw and protective device.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A kit for use in securing a tissue graft to a bone, comprising:
one or more interference screws designed to hold a tissue graft within a bone tunnel, at least one of the one or more interference screws comprising:
a threaded body extending along a central axis and including raised threads for threadable insertion into a bone tunnel, the threaded body including an obliquely angled face disposed at a proximal end of the threaded body so that the raised threads at the proximal end of the threaded body are discontinuous, and one or more protective devices for temporarily mating with at least one of the one or more interference screws during insertion of the interference screw into a bone tunnel and that are configured so as to be detachable from the interference screw after securing a tissue graft to a bone in order to not permanently remain in the bone tunnel along with the interference screw, each protective device comprising:

a body having an angled face that corresponds to and is configured to abut the angled face of at least one of the one or more interference screws when the protective device is concentrically aligned with the interference screw about the central axis in order to reduce or eliminate the tendency of the discontinuous raised threads at the proximal end of the threaded body to snag a tissue graft and/or sutures when the interference screw is screwed into a bone tunnel, at least one of the protective devices further comprising a threaded portion having discontinuous raised threads adjacent to the angled face that are configured to align with corresponding discontinuous raised threads disposed on at least one of the one or more interference screws when the protective device is concentrically aligned with the interference screw and the face of the protective device abuts the face of the interference screw, the discontinuous raised threads of the at least one protective device thereby completing the discontinuous raised threads of the at least one interference screw.

2. A kit as defined in claim 1, the angled faces of the protective device and the interference screw having normalized angles relative to the central axis that together add up to 90°.

3. A kit as defined in claim 1, the angled face of at least one of the one or more protective devices having a normalized angle relative to the central axis in a range of about 30° to about 70°.

4. A kit as defined in claim 1, the angled face of at least one of the one or more protective devices having a normalized angle relative to the central axis in a range of about 50° to about 60°.

5. A kit as defined in claim 1, at least one of the one or more protective devices including threads having a pitch and spacing that are substantially similar to the pitch and spacing of threads of at least one of the one or more interference screws.

6. A kit as defined in claim 1, at least one of the one or more protective devices including a threaded portion having a diameter that is substantially equal to the diameter of at least one of the one or more interference screws.

7. A kit as defined in claim 1, at least one of the one or more protective devices including a threaded portion having an external diameter of at least about 10 mm.

8. A kit as defined in claim 1, at least one of the one or more protective devices further comprising a threaded portion and a non-threaded portion that is adjacent to the threaded portion and distal to the angled face.

9. A kit as defined in claim 1, at least one of the one or more protective devices further comprising a passageway through the body along the central axis, the passageway sized and configured so as to permit a shaft of a driver that is configured to mechanically engage the one or more interference screws through the passageway.

10. A kit as defined in claim 9, the passageway being sized and configured so that the protective device can freely rotate relative to the driver when the shaft is disposed through the passageway.

11. A kit as defined in claim 9, the passageway being sized and configured so as to mechanically engage the driver when a shaft of the driver is disposed through the passageway.

12. A kit as defined in claim 1, the kit comprising:

a plurality of interference screws, at least two of which are differently-sized; and a plurality of protective devices sized and configured so that there is at least one protective device that corresponds to each interference screw.

13. A kit as defined in claim 1, further comprising at least one driver that is configured to mechanically engage a corresponding hole in one or more of the interference screws.

14. A kit as defined in claim 13, each protective device further comprising a passageway through the body that is sized and configured so as to permit a shaft of the driver to pass through the passageway so as to permit the shaft of the driver to engage a corresponding hole of an interference screw when the protective device is mated with a corresponding interference screw.

15. A kit as defined in claim 14, the passageway being sized and configured so as to mechanically engage the driver when the shaft is disposed through the passageway.

16. A method of introducing an interference screw into a bone tunnel, comprising:

(a) obtaining an interference screw that is sized and configured so as to engage bone tissue surrounding the bone tunnel with a desired level of pressure, the interference screw having a threaded body disposed along a central axis, an angled face disposed at an end of the threaded body, and a hole configured to mechanically engage a shaft of a driver;

(b) obtaining a protective device comprising a body having a passageway through which a shaft of a driver can pass and an angled face that is configured to engage the angled face of the interference screw when the protective device is concentrically aligned with the interference screw;

(c) inserting a shaft of a driver through the passageway of the protective device and into the hole of the interference screw in order for the driver to mechanically engage the interference screw and concentrically align it with the protective device;

(d) introducing the interference screw into a bone tunnel by rotating the driver and causing the interference screw to rotate about the central axis while the angled face of the protective device is adjacent to the angled face of the interference screw; and (e) removing the protective device, the interference screw remaining in the bone tunnel after removal of the protective device.

17. A method as defined in claim 16, the protective device including threads that complete a discontinuity in the threads of the interference screw.

* * * * *

UNITED STATES PATENT AND TRADEMARK OFFICE
CERTIFICATE OF CORRECTION

PATENT NO.         : 7,235,078 B2
APPLICATION NO. : 10/304719
DATED                  : June 26, 2007
INVENTOR(S)       : Hugh S. West, Jr.

Page 1 of 1

It is certified that error appears in the above-identified patent and that said Letters Patent is hereby corrected as shown below:

Title Page
Page 2, Item 56, change "Reay-Young et al" to --Seyr et al--

Column 7
Line 5, change "comprises" to --comprise--
Line 11, after "comprise" insert --of poly-l-lactic acid--

Column 9
Line 60, change "fight" to --fit--
Line 62, change "same" to --some--

Column 10
Line 33, after "configured" insert --to--

Signed and Sealed this

Fourth Day of December, 2007

JON W. DUDAS
*Director of the United States Patent and Trademark Office*